United States Patent [19]

Okawa et al.

[11] Patent Number: 5,403,881

[45] Date of Patent: Apr. 4, 1995

[54] ROOM-TEMPERATURE-CURABLE COMPOSITION

[75] Inventors: Tadashi Okawa; Shigeki Sugiyama; Shuji Yamada, all of Chiba, Japan

[73] Assignee: Dow Corning Toray Silicone Co., Ltd., Tokyo, Japan

[21] Appl. No.: 141,459

[22] Filed: Oct. 22, 1993

[30] Foreign Application Priority Data

Nov. 30, 1992 [JP] Japan ................................. 4-343174

[51] Int. Cl.[6] ............................................. C08K 5/24
[52] U.S. Cl. ...................................... 524/261; 524/268; 524/425; 524/588; 524/788; 525/403; 528/33; 528/34
[58] Field of Search ............... 524/261, 268, 425, 588, 524/788; 525/403; 528/17, 33, 34

[56] References Cited

U.S. PATENT DOCUMENTS

| | | | |
|---|---|---|---|
| 4,618,646 | 10/1986 | Takago et al. | 524/788 |
| 4,888,404 | 12/1989 | Klosowski et al. | 528/34 |
| 5,013,800 | 5/1991 | Inoue | 528/34 |

FOREIGN PATENT DOCUMENTS

| | | | |
|---|---|---|---|
| 73998 | 6/1977 | Japan . | |
| 115456 | 7/1982 | Japan . | |
| 3-294355 | 12/1991 | Japan | 524/788 |

*Primary Examiner*—John C. Bleutge
*Assistant Examiner*—Mark D. Sweet

*Attorney, Agent, or Firm*—Roger H. Borrousch

[57] ABSTRACT

A room-temperature-curable composition is very storage stable under seal at room temperature, cures to give a rubbery elastic material with excellent physical properties, and is useful as a sealant composition when polyoxyalkylene has at the terminals groups of the formula

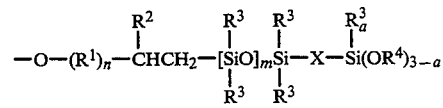

of which one example of a organosiloxane-modified polyoxyalkylene is

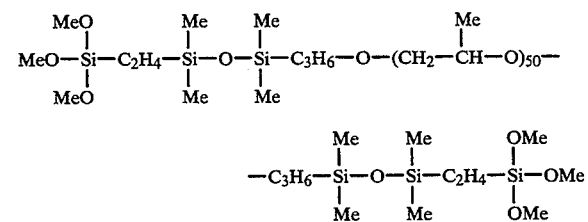

in which Me is methyl.

18 Claims, No Drawings

ROOM-TEMPERATURE-CURABLE COMPOSITION

BACKGROUND OF THE INVENTION

1. Technical Field

The present invention relates to a room-temperature-curable composition. More specifically, the present invention relates to a room-temperature-curable composition that has an excellent storage stability under seal at room temperature and that is useful as a sealant composition.

2. Prior Art and Problem to Be Solved by the Invention

One example of a room-temperature-curable sealant composition is the composition disclosed in Japanese Patent Application Laid Open [Kokai or Unexamined] Number Sho 52-73998 [73,998/1977], published Jun. 21, 1977. The base component in this composition is a polymer that has a polyoxyalkylene main chain and silicon-bonded methoxy in terminal position. A drawback to this room-temperature-curable sealant composition is that its weathering resistance is inferior to that of silicone sealant compositions.

Japanese Patent Application Laid Open Number Sho 57-115456 [115,456/1982], published Jul. 17, 1982, discloses a room-temperature-curable composition whose base component is a copolymer in which polyoxyalkylene is bonded across a divalent organic group to organopolysiloxane having terminal-position Si-bonded hydrolyzable groups. However, the copolymer that is the base component of this composition contains a siloxane bond adjacent to hydrolyzable group-bearing silicon and is therefore very susceptible to attack by nucleophiles. As a result, the room-temperature-curable composition based on this copolymer has a poor storage stability under seal.

SUMMARY OF THE INVENTION

The inventors conducted extensive research in order to solve the problem described above. As a result, with regard to a copolymer in which polyoxyalkylene is bonded across a divalent organic group to organopolysiloxane (or organosiloxane) having terminal- position Si-bonded alkoxy groups, the inventors discovered that the substitution of a divalent organic group for the oxygen atom in the siloxane bond at the end of the organopolysiloxane (or organosiloxane) chain yields a copolymer that can be formulated into a room-temperature-curable composition having a substantially improved storage stability under seal. The present invention was developed based on this discovery.

The present invention takes as its object the introduction of a room-temperature-curable composition that is very storage stable under seal at room temperature and that cures to give a rubbery elastic material with excellent physical properties.

This invention relates to a room-temperature-curable composition comprising (A) 100 weight parts of a organosiloxane-modified polyoxyalkylene that has a molecular weight of 500 to 16,000, whose main chain is constituted of the unit with the formula —RO— in which R is an alkylene group having 1 to 4 carbon atoms, and that has the group with the following formula in molecular chain terminal position

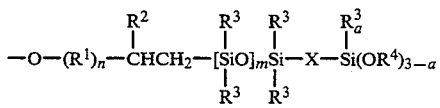

in which $R^1$ is a divalent hydrocarbon group, $R^2$ is the hydrogen atom or a monovalent hydrocarbon group, $R^3$ and $R^4$ are monovalent hydrocarbon groups, X is a divalent organic group, a is 0, 1, or 2, m is a number with a value of at least 1, and n is 0 or 1; (B) 0.1 to 50 weight parts of an $Si_{1-20}$ silicon compound that contains at least 2 silicon-bonded alkoxy groups in each molecule; (C) a condensation-reaction catalyst in a quantity sufficient to cure the composition; and (D) 0 to 250 weight parts of an inorganic filler.

DETAILED DESCRIPTION OF THE PREFERRED EMBODIMENTS

Component (A) is the main or base component of tile composition of the present invention, and it is a organosiloxane-modified polyoxyalkylene that has a main chain constituted of the —RO— unit and that has the group with the following formula in molecular chain terminal position:

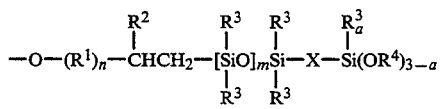

R is a $C_1$-$C_4$ alkylene group and is exemplified by methylene, ethylene, 1-methylethylene, 1-ethylethylene, and 1,1-dimethyl-ethylene. $R^1$ in the preceding formula is a divalent hydrocarbon group and is exemplified by methylene, ethylene, propylene, and butylene. $R^2$ is the hydrogen atom or a monovalent hydrocarbon group, and the latter is exemplified by alkyl groups such as methyl, ethyl, and propyl; cycloalkyl groups such as cyclohexyl; aryl groups such as phenyl, tolyl, and xylyl; and aralkyl groups such as benzyl and phenethyl. $R^3$ and $R^4$ in each case are monovalent hydrocarbon groups as defined for $R^2$. The group X in the preceding formula is a divalent organic group and is exemplified by methylene, ethylene, propylene, butylene, phenylene, and substituted phenylene. The subscripts in the preceding formula have the following values: a=0, 1, or 2; m is a number with a value of at least 1; and n =0 or 1. This component has a molecular weight of 500 to 16,000. Component (A) can be synthesized by an addition reaction between SiH-containing organosiloxane or SiH-containing organopolysiloxane with the following formula

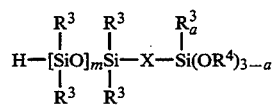

wherein $R^3$, $R^4$, X, m, and a are defined as above, and polyoxyalkylene (molecular weight=400 to 15,000) that contains in each molecule in molecular chain terminal position at least 1.1 unsaturated groups with the formula

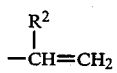

wherein $R^2$ is defined as above.

Component (B) is an $Si_{1-20}$ silicon compound that contains at least 2 silicon-bonded alkoxy groups in each molecule. Component (B) is used (i) to adjust properties such as the tensile strength and elongation in the cured product afforded by the composition of the present invention and (ii) to improve the adherence of the cured product. Component (B) is exemplified by silanes such methyltrimethoxysilane, vinyltrimethoxysilane, phenyltrimethoxysilane, tetramethoxysilane, gamma-methacryloxypropyltrimethoxysilane, gamma-glycidoxypropyl-trimethoxysilane, gamma-aminopropyltrimethoxysilane, and so forth. Component (B) is also exemplified by branched, cyclic, and linear $Si_{1-20}$ silicon compounds that contain at least two silicon-bonded alkoxy groups in each molecule.

Component (B) is added to the composition at 0.1 to 50 weight parts per 100 weight parts component (A) and preferably at 1 to 10 weight parts per 100 weight parts component (A).

Operable for the condensation-reaction catalyst comprising component (C) are the known silanol condensation-reaction catalysts including titanium catalysts such as alkyl titanate esters; organosilicon titanates; and titanium chelate compounds such as diisopropoxytitanium bis(acetylacetone); metal carboxylates such as tin octylate, dibutyltin dilaurate, dibutyltin diacetate, and dibutyltin phthalate; and other acid catalysts and base catalysts.

Component (C) should be added to the composition in a quantity sufficient to effect curing of the composition of the present invention. It is added, in general, at 0.1 to 20 weight parts per 100 weight parts component (A) and is preferably added at 0.1 to 10 weight parts per 100 weight parts component (A).

The inorganic filler comprising component (D) is used on an optional basis to improve various physical properties of the composition of the present invention. Operable fillers are exemplified by known inorganic fillers such as fumed silica, precipitated silica, quartz powder, carbon black, calcium carbonate, diatomaceous earth, clay, talc, titanium oxide, alumina, bentonite, zinc oxide, ferric oxide, active zinc white, shirasu balloons, asbestos, glass fiber, and so forth.

Component (D) is added at 0 to 250 weight parts per 100 weight parts component (A) and preferably at 10 to 200 weight parts per 100 weight parts component (A).

The composition of the present invention is prepared by mixing the specified quantities of components (A) through (C) or (A) through (D) as described hereinbefore by a known mixing means. In addition to the preceding components, the composition of the present invention may also contain the various additives known in the art, for example, plasticizers, colorants such as pigments and so forth, heat stabilizers, cold- resistance improvers, flame retardants, thixotropy agents, dehydrating agents, antimicrobials, adhesion promoters, and so forth.

The composition of the present invention as described hereinbefore has an excellent storage stability at room temperature under seal. Moreover, this composition cures upon contact with moisture to yield a rubbery elastic cured material that exhibits an excellent weathering resistance. The composition of the present invention is therefore very useful as a sealant composition for buildings, ships, automobiles, roads, and so forth.

The present invention will be explained below in greater detail through working examples, in which parts indicates weight parts.

REFERENCE EXAMPLE 1

138.5 g (1013.5 millimoles) 1,1,3,3-tetramethyldisiloxane was mixed with a platinum/1,3-divinyltetramethyldisiloxane complex so as to give 20 ppm platinum metal based on the total weight of the reaction mixture, and the mixture was heated to 80° C. 50 g (337.8 millimoles) vinyltrimethoxysilane was dripped into the mixture, and heating under reflux was continued for an additional 1 hour after tile completion of this addition. The reaction mixture was then sampled and analyzed by gas chromatography (GLC): the vinyltrimethoxysilane peak had disappeared, which confirmed completion of the reaction. After the excess 1,1,3,3-tetramethyldisiloxane had been distilled out by heating at ambient pressure, vacuum distillation yielded 62.1 g of a fraction at 65.5° C.69° C./133.3 Pa. The results of infrared absorption spectral analysis (IR) and nuclear magnetic resonance analysis (NMR) confirmed this fraction to be organosiloxane with the following structural formula.

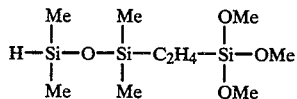

REFERENCE EXAMPLE 2

The following were mixed and heated to 80° C.: 100 g (33.3 millimoles) polyoxypropylene (average molecular weight =3,000) bearing the allyloxy group at both terminals, 100 mL toluene, and sufficient platinum/1,3-divinyltetramethyldisiloxane complex to give 20 ppm platinum metal based on the total weight of the reaction mixture. 19.7 g (70.0 millimoles) of the organosiloxane synthesized in Reference Example 1 was then dripped into the mixture, and heating under reflux was continued for an additional 3 hours after the completion of this addition. The reaction mixture was then sampled and analyzed by NMR: the vinyl group absorption had disappeared, which confirmed completion of the reaction. Removal of the low boilers by vacuum distillation with heating yielded 116.9 g of a polymer. The results of IR and NMR analyses confirmed this polymer to be organosiloxane-modified polyoxypropylene with tile following structural formula.

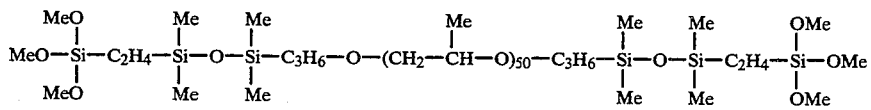

REFERENCE EXAMPLE 3

42.8 g organosiloxane was prepared as in Reference Example 1, but in this case using 90.0 g (668.2 millimoles) 1,1,3,3-tetramethyldisiloxane and also replacing the vinyltrimethoxysilane with 30.0 g (222.7 millimoles) vinylmethyldimethoxysilane. This organosiloxane was confirmed by IR and NMR analyses to have the following structural formula.

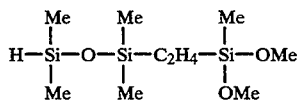

REFERENCE EXAMPLE 4

116.8 g, polymer was prepared as in Reference Example 2, but in this case using 18.62 g (70.0 millimoles) of the organosiloxane synthesized in Reference Example 3 in place of the organosiloxane synthesized in Reference Example 1. The results of IR and NMR analyses confirmed this polymer to be organosiloxane-modified polyoxypropylene with the following structural formula.

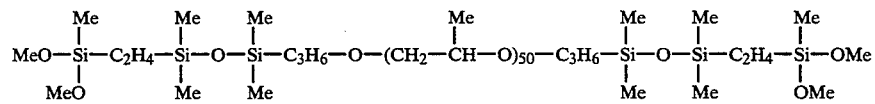

116.8 g polymer was prepared as in Reference Example 2, but in this case using 18.9 g (70.0 millimoles) 1,1,3,3-tetramethyl-5,5,5-trimethoxytrisiloxane in place of the organosiloxane synthesized in Reference Example 1. The results of IR and NMR analyses confirmed this polymer to be organosiloxane-modified polyoxypropylene with the following structural formula.

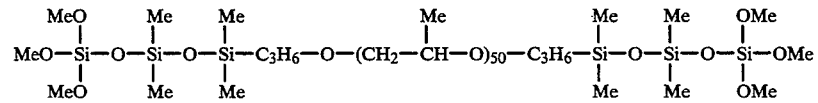

EXAMPLE 1

A room-temperature-curable composition was prepared by mixing the following: 100 parts of the organosiloxane-modified polyoxypropylene prepared in Reference Example 2, 150 parts precipitated calcium carbonate, 5 parts methyltrimethoxysilane, and 2 parts diisopropoxytitanium bis(acetylacetone). This composition was filled and sealed into aluminum tubes. The composition was then discharged from a tube, molded into a 2 mm-thick sheet, and cured in a 20° C./60% RH ambient. After 7 days the physical properties of the cured product were measured in accordance with JIS K 6301. In addition, a composition-filled tube was held in a 50° C. oven for 8 weeks, and the composition was then cured as above and the physical properties of the cured material were measured as above. The measurement results were as reported in Table 1. The measurement results confirmed that this composition had an excellent storage stability under seal.

EXAMPLE 2

A room-temperature-curable composition was prepared as in Example 1, but in this case using the organosiloxane-modified polyoxypropylene synthesized in Reference Example 4 in place of the organosiloxane-modified polyoxypropylene synthesized in Reference Example 2 that was used in Example 1. The physical properties of this composition were measured as in Example 1, and these results were as reported in Table 1. These measurement results confirmed that this composition exhibited an excellent storage stability under seal.

COMPARISON EXAMPLE 1

A room-temperature-curable composition was prepared as in Example 1, but in this case using the organosiloxane-modified polyoxypropylene synthesized in Reference Example 5 in place of the organosiloxane-modified polyoxypropylene synthesized in Reference Example 2 that was used in Example 1. The physical properties of this composition were measured as in Example 1, and these results were as reported in Table 1. These measurement results confirmed that tile instant composition exhibited a storage stability under seal that was substantially inferior to that of the compositions in Example 1 and Example 2.

TABLE 1

|  | HARDNESS (JIS A) | | TENSILE STRENGTH ($kg/cm^2$) | | ELONGATION (%) | |
| --- | --- | --- | --- | --- | --- | --- |
|  | Initial | After 8 weeks | Initial | After 8 weeks | Initial | After 8 weeks |
| Example 1 | 50 | 45 | 24 | 19 | 400 | 380 |
| Example 2 | 39 | 35 | 20 | 16 | 300 | 280 |
| Comp. | 46 | 9 | 21 | 3 | 300 | 25 |
| Example 1 | | | | | | |

EFFECTS OF THE INVENTION

The room-temperature-curable composition of the present invention is characterized by its excellent storage stability under seal at room temperature and by its ability to cure into a rubbery elastic material with excellent physical properties.

That which is claimed is:

1. A room-temperature-curable composition comprising
   (A) 100 weight parts of a organosiloxane-modified polyoxyalkylene whose main chain is constituted of the unit with the formula —RO— in which R is an alkylene group having 1 to 4 carbon atoms, and that has the group with the following formula in molecular chain terminal position

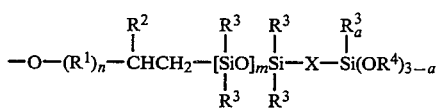

in which $R_1$ is a divalent hydrocarbon group, $R_2$ is the hydrogen atom or a monovalent hydrocarbon group, $R^3$ and $R^4$ are monovalent hydrocarbon groups, X is a divalent organic group, a is 0, 1, or 2, m is a number with a value of at least 1, and is 0 or 1;

(B) 0.1 to 50 weight parts of an $Si_{1-20}$ silicon compound that contains at least 2 silicon-bonded alkoxy groups in each molecule;

(C) a condensation-reaction catalyst in a quantity sufficient to cure the composition; and (D) 0 to 250 weight parts of an inorganic filler.

2. The room-temperature-curable composition according to claim 1 in which (B) is present in an amount of from 1 to 10 weight parts, (C) is present in an amount of from 0.1 to 10 weight parts, and (D) is present in an amount of from 10 to 200 weight parts.

3. The room-temperature-curable composition according to claim 1 in which each $R^2$, $R^3$, and $R^4$ is methyl, X is ethylene, a is 3, and n is 0.

4. The room-temperature-curable composition according to claim 2 in which each $R^2$, $R^3$ and $R^4$ is methyl, X is ethylene, a is 3 and n is 0.

5. The room-temperature-curable composition according to claim 1 in which each $R^2$, $R^3$, and $R^4$ is methyl, X is ethylene, a is 2, and n is 0.

6. The room-temperature-curable composition according to claim 2 in which each $R^2$, $R^3$, and $R^4$ is methyl, X is ethylene, a is 2, and n is 0.

7. The room-temperature-curable composition according to claim 3 in which the catalyst of (C) is a titanium catalyst.

8. The room-temperature-curable composition according to claim 4 in which the catalyst of (C) is a titanium catalyst.

9. The room-temperature-curable composition according to claim 5 in which the catalyst of (C) is a titanium catalyst.

10. The room-temperature-curable composition according to claim 6 in which the catalyst of (C) is a titanium catalyst.

11. The room-temperature-curable composition according to claim 7 in which (B) is methyltrimethoxysilane and (D) is calcium carbonate.

12. The room-temperature-curable composition according to claim 8 in which (B) is methyltrimethoxysilane and (D) is calcium carbonate.

13. The room-temperature-curable composition according to claim 9 in which (B) is methyltrimethoxysilane and (D) is calcium carbonate.

14. The room-temperature-curable composition according to claim 10 in which (B) is methyltrimethoxysilane and (D) is calcium carbonate.

15. The room-temperature-curable composition according to claim 11 in which (C) is diisoproxytitanium bis(acetyl-acetone).

16. The room-temperature-curable composition according to claim 12 in which (C) is diisoproxytitanium bis(acetyl-acetone).

17. The room-temperature-curable composition according to claim 13 in which (C) is diisoproxytitanium bis(acetyl-acetone).

18. The room-temperature-curable composition according to claim 14 in which (C) is diisoproxytitanium bis(acetyl-acetone).

* * * * *